US00PP26049P3

(12) United States Plant Patent
Koike

(10) Patent No.: US PP26,049 P3
(45) Date of Patent: Nov. 3, 2015

(54) BUNASHIMEJI MUSHROOM PLANT NAMED 'MARMO SHIRO-2'

(50) Latin Name: *Hypsizygus marmoreus*
Varietal Denomination: marmo shiro-2

(71) Applicant: HOKUTO CORPORATION, Nagano (JP)

(72) Inventor: Ayumi Koike, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 259 days.

(21) Appl. No.: 13/815,862

(22) Filed: Mar. 15, 2013

(65) Prior Publication Data

US 2014/0130222 P1 May 8, 2014

(30) Foreign Application Priority Data

Mar. 28, 2012 (JP) ..... 26865

(51) Int. Cl.
*A01H 5/04* (2006.01)
*A01H 15/00* (2006.01)

(52) U.S. Cl.
USPC ..... Plt./394
CPC ..... *A01H 15/00* (2013.01)

(58) Field of Classification Search
USPC ..... Plt./394
CPC ..... A01H 15/00; A01H 5/04
See application file for complete search history.

(56) References Cited

U.S. PATENT DOCUMENTS

PP16,294 P3 2/2006 Ishii et al.

*Primary Examiner* — Kent L Bell
(74) *Attorney, Agent, or Firm* — Konomi Takeshita

(57) ABSTRACT

The present variety of mushroom plant named 'marmo shiro-2' was cultivated by the gathering and repeated breeding of Bunashimeji mushrooms having dominant traits, which has good qualitative characteristics and appearance, less adhesion of the stem, excellent keeping qualities and storage life, and improved after-storage taste. This edible mushroom is exquisite in stability, reproducibility and uniformity when being produced.

5 Drawing Sheets

BACKGROUND OF THE INVENTION

This invention relates to a new and distinct variety of mushroom plant of Bunashimeji mushroom, *Hypsizygus marmoreus* (Peck) Bigelow. This new variety named 'marmo shiro-2' cultivated by repeated breeding of Bunashimeji mushrooms having dominant traits, which has less adhesion of stem, excellent keeping quality and improved after-storage taste and ensure presentable stability, reproducibility and uniformity.

Bunashimeji (*Hypsizygus marmoreus*) now boasts of being the second most consumed edible mushroom after enokitake mushroom. Ever since bunashimeji was cultivated and began to be sold in large quantities in the market, its characteristic bitter taste had been a matter of concern. Consequently, 'Hokuto-8 strain', whose bitterness has been reduced to an imperceptible level, was developed to develop a tasty Bunashimeji mushroom. Investigation on tasty bunashimeji was continued even after the development of 'Hokuto-8', and a variety with better taste, quality and keeping quality named 'Hokuto-18 strain' was developed, which contributed to increase in consumption. However, most of the naturally growing mushrooms that are popular in Japan from the olden days are collected at the beginning of autumn, due to which one generally forms an image of autumn and winter when the word mushroom is heard. We started working on the development of a new variety of mushroom that can be used with bright-colored vegetables of summer in salad and other recipes since we can stably supply them throughout the year by growing under protected conditions. As a result, the 'Hokuto shiro-1 strain' mushroom that has refreshing whiteness and jellylike food texture was developed and patented in US (U.S. Plant Pat. No. 16,294 P3).

In order to further improve the stability of cultivation and quality of mushrooms, selective breeding was repeatedly carried out by cross-breeding. As a result, the 'marmo shiro-2 strain' that has the whiteness and food-texture of 'Hokuto shiro-1', as well as the quality and keeping quality of 'Hokuto-18' was developed. Subsequently, the stability, reproducibility and uniformity of the variety were verified, and cultivation was completed.

SUMMARY OF THE INVENTION

The present invention is a new and distinct variety of mushroom characterized particularly by its good qualitative character and appearance, good keeping quality and storage life and delicious tasting, which can be cultivated by gathering and repeated breeding of fungal strains having dominant traits and is exquisite in stability, reproducibility and uniformity when being produced. This novel and distinct variety of mushroom is identified as 'marmo shiro-2'.

DETAILED DESCRIPTION OF THE INVENTION

The history of the 'marmo shiro-2' mushroom in terms of improvement period and the like are set forth in the following chronological list of each stage of variety improvement:

October 2001: Cultivation of 'Hokuto shiro-1 strain'

October 2003: Cultivation of 'Hokuto 18 strain'

November 2006: Cultivation of 'MH025464'

September 2009: 'Hokuto shiro-1' and 'MH025464' were crossed and the strains with white cap which are to be kept were picked from the obtained strains, and considered as 'MH025465'.

September 2010: 'Hokuto-18 strain' and 'MH025465' were crossed and an excellent strain that fulfill the cultivation objective (test number 10HM395) was obtained. Then, growing test was repeatedly conducted and the distinguishability, stability and uniformity were confirmed, upon which the strain was named 'marmo shiro-2' and cultivation was completed.

March 2012: Applied for registration of new variety to Ministry of Agriculture, Forestry and Fisheries of Japan.

The 'marmo shiro-2' mushroom has the following characteristics: less adhesion of stem, excellent keeping quality and improved after-storage taste.

(1) Comparison with Existing Varieties by Dual Culture

Formation of zone line in the varieties similar to 'marmo shiro-2' and parental varieties were studied by conducting dual culture.

Study Method:

The 'marmo shiro-2' and another strain were co-inoculated with an interval of 3 cm by using potato dextrose agar culture medium. Then, the formation of zone line was determined by culturing for 28 days at 25° C.

Strain Used:

'marmo shiro-2': Present variety

'Hokuto shiro-1 strain': Varieties similar to the present variety

'Hokuto-18 strain': Parental variety of the present variety

Figure 1B:
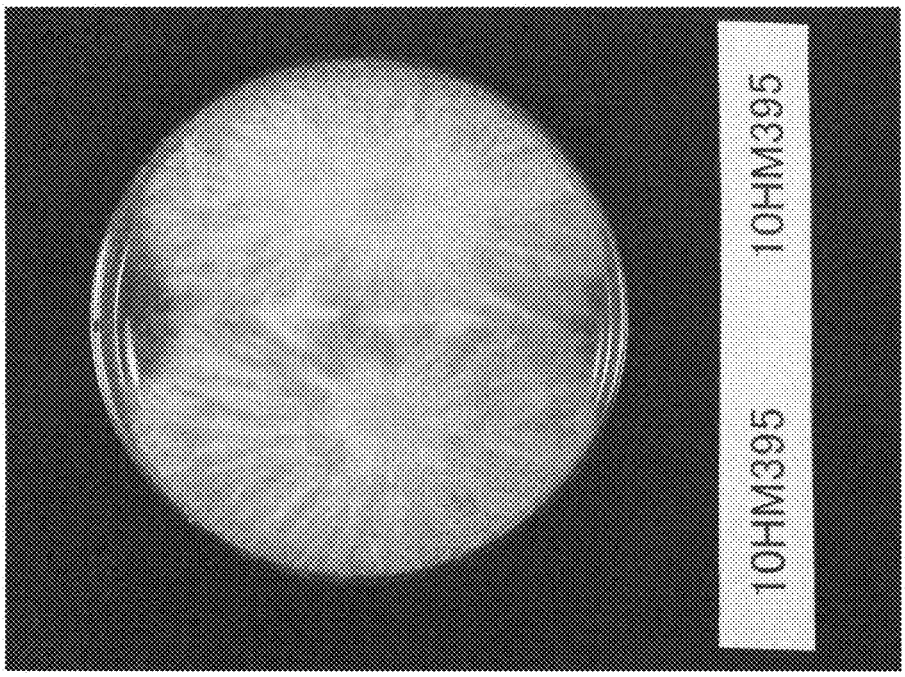
FIGS. 1A and 1B respectively show front and back images of a dual-culture of 'marmo shiro-2' colony.
Figure 1A:
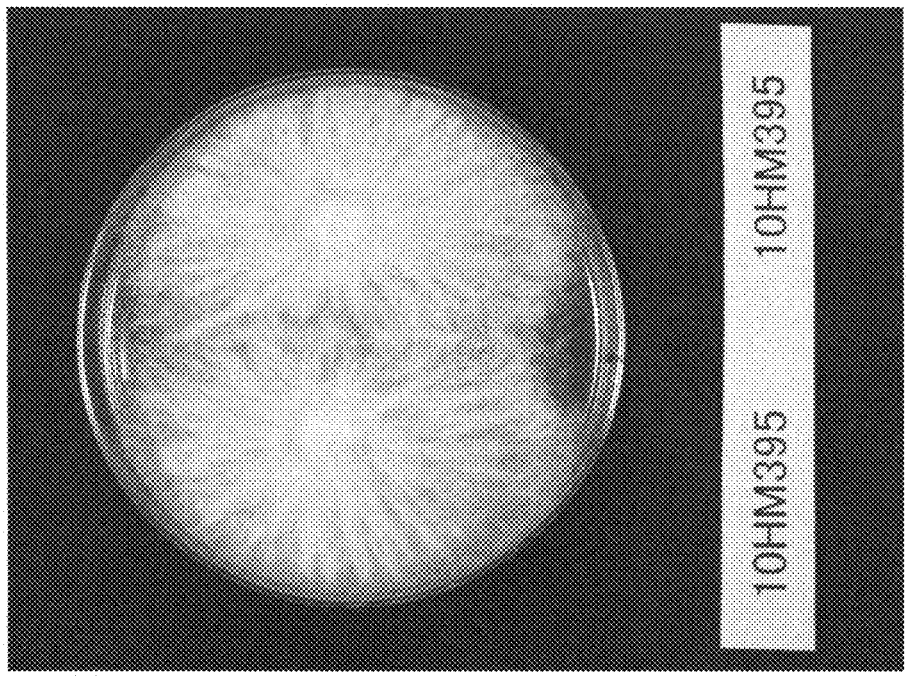
Figure 2B:
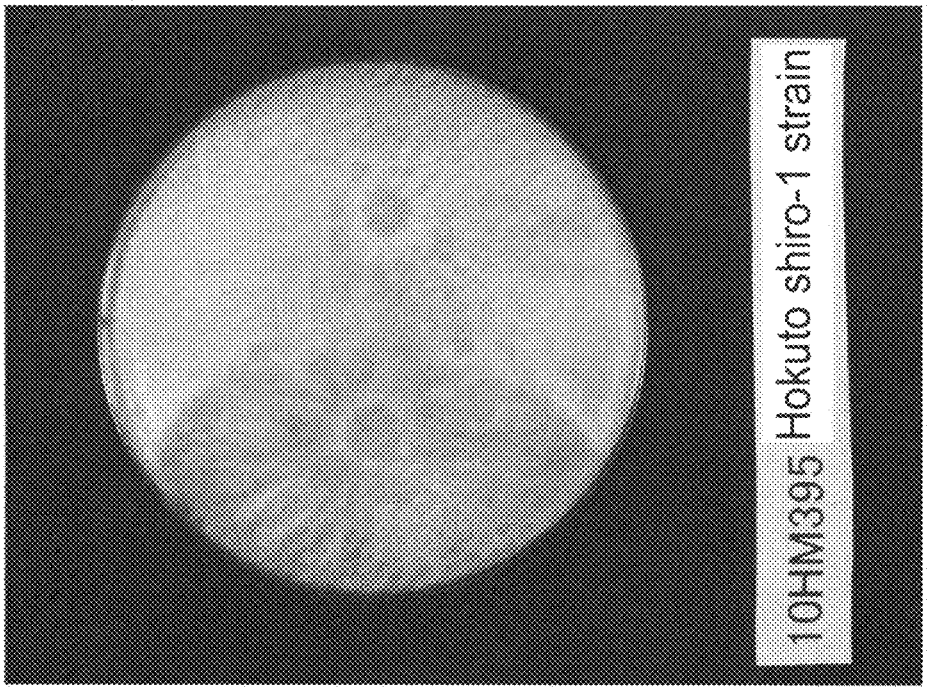
FIGS. 2A and 2B respectively show front and back images of a dual-culture of 'marmo shiro-2' and 'Hokuto shiro-1' strains.
Figure 2A:
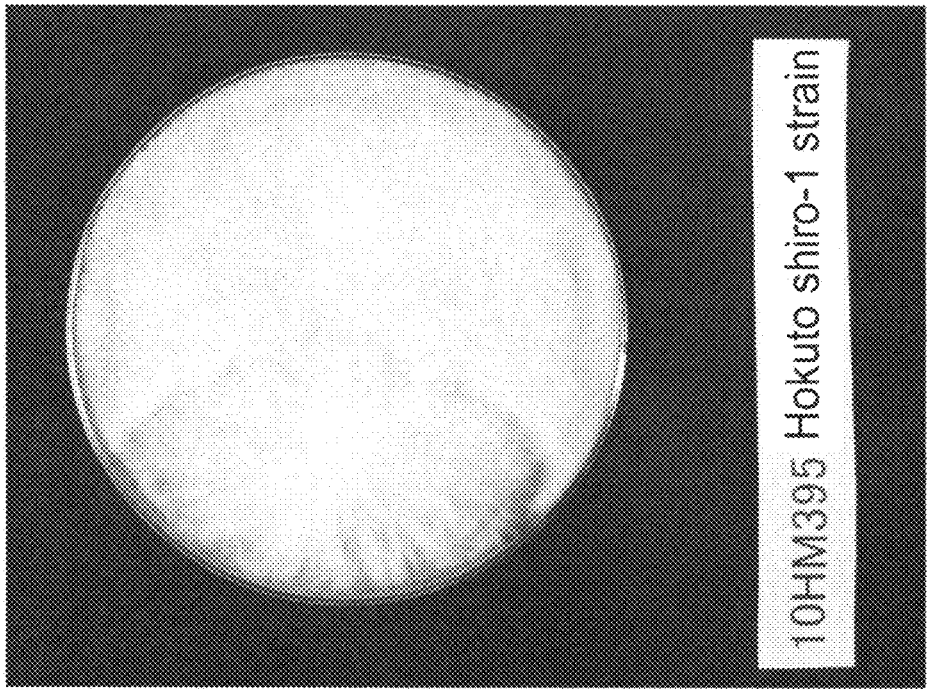
Figure 3B:
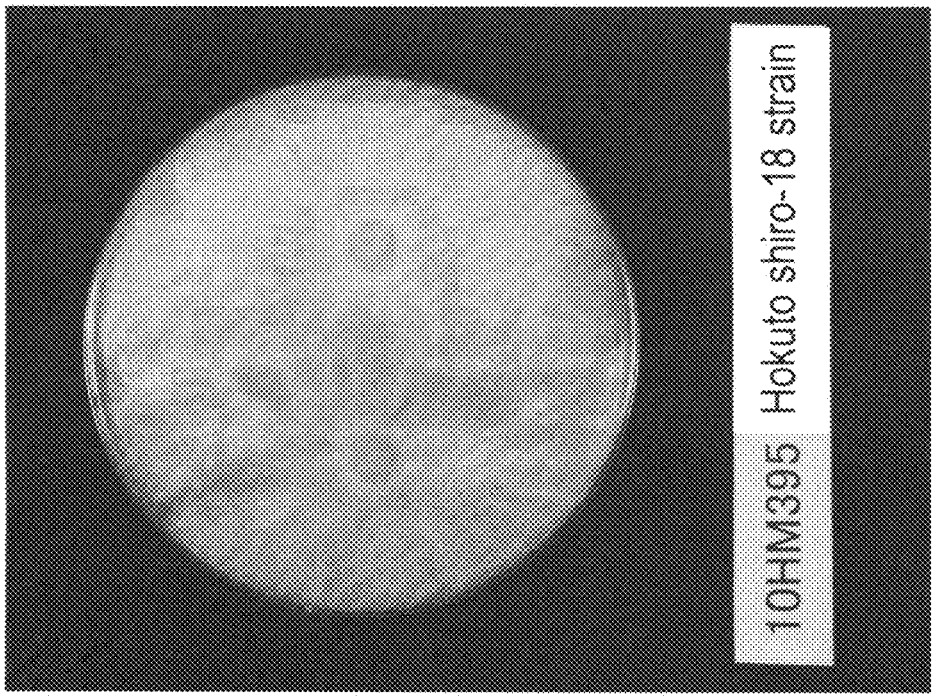
FIGS. 3A and 3B respectively show front and back images of a dual-culture of 'marmo shiro-2' and 'Hokuto-18' strains.
Figure 3A:
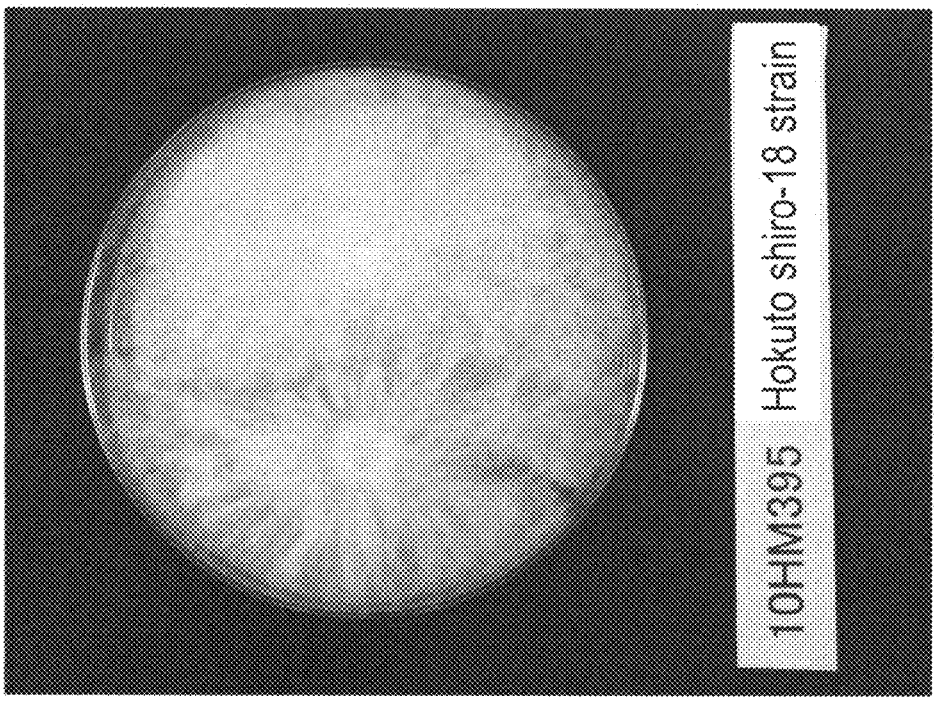

Results:

Zone lines were formed between 'marmo shiro-2' and all other co-cultured varieties (Table 1, FIGS. 1 to 3). These results show that this strain is a new variety.

TABLE 1

| | Results of dual culture | |
|---|---|---|
| | Similar variety | |
| | Hokuto shiro-1 strain | Hokuto-18 strain |
| marmo shiro-2 | + | + |

* No zone line was seen in the dual culture of 'marmo shiro-2 strains'.

(2) Culture Characteristics of 'marmo shiro-2'

After inoculating a piece of agar of 'marmo shiro-2' with 5 mm diameter in potato dextrose agar, preliminary culture was carried out for 4 days at 25° C. and hyphae were regenerated (about 10 mm diameter). Then, it was cultured for 7 days at 5-30° C. with 5° C. interval. When the mean hyphae growth speed per day was calculated from the hyphae growth speed of 7-day culture, it was found that the mean hyphae growth rate was somewhat slow at 20° C. and 25° C. (See Table 2).

(3) Morphological Characteristics Based on an Example of Cultivating 'marmo shiro-2'

Cultivation Method:

Container: An 850 polypropylene bottle (Capacity: 850 ml, mouth diameter: 58 mm) was used.

Culture medium: Conifer sawdust, corn-cob, rice bran and wheat bran were mixed in the dry-weight ratio of 7:3:8:2, and the mixture was adjusted to 65% water content. The culture medium was filled up to the brim of bottle at the rate of 540±20 g per bottle, and was sterilized at high pressure.

Starter culture: 20 ml of sawdust culture was inoculated per bottle.

Culture: 50-90 days culturing was conducted under 22° C. temperature and 70% humidity.

Development: After incubation, the cultivar was shifted to a growing room after Kinkaki (removing the original inoculum mechanically). Development was conducted under 15±1° C. temperature and 95% or more humidity. The cultivar is not exposed to light particularly in the first 14 days. After the 14th day, about 500-1,000 Lx is taken and development is conducted at about 2,000 ppm $CO_2$ density. The mushroom is harvested when the cap in the center of the stump has fully opened.

Cultivation Results:

The characteristics of 'marmo shiro-2' cultivated under the conditions mentioned above, and the specific difference in characteristics with the most similar variety are explained in Table 2 below.

Figure 4:
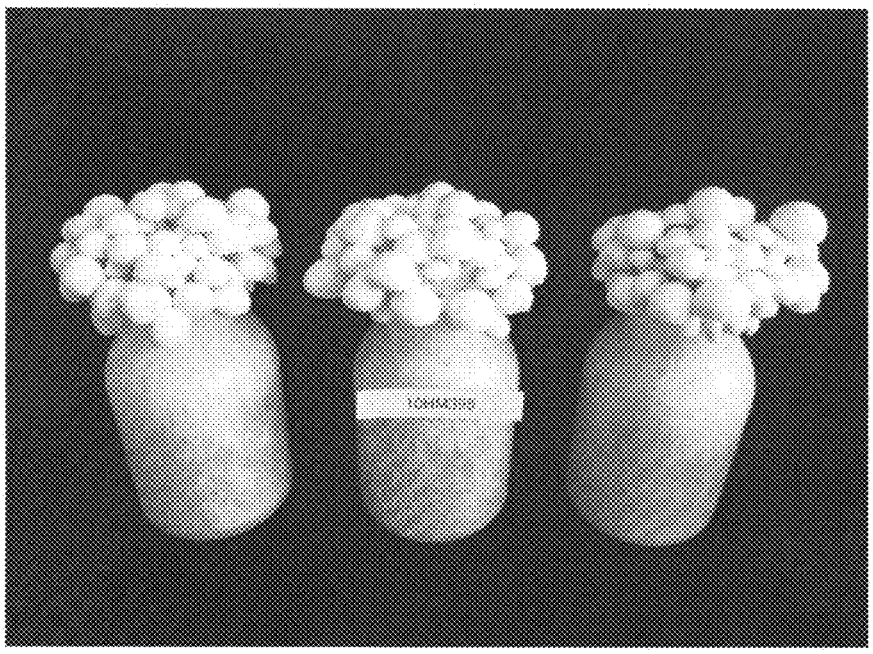
FIG. 4 shows an image of a fruit body of 'marmo shiro-2'.
Figure 5:
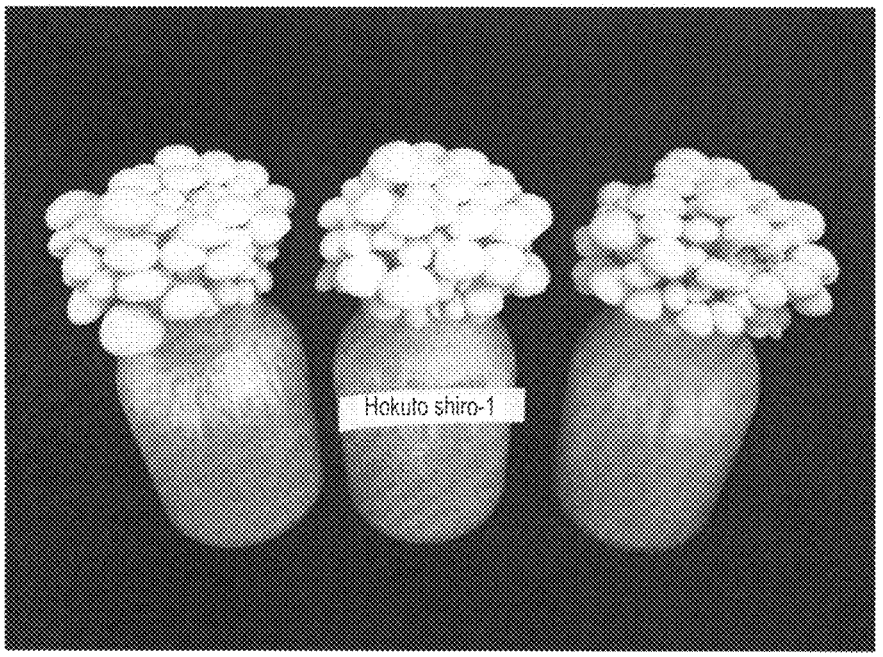
FIG. 5 shows an image of a fruit body of 'Hokuto shiro-1'.
Figure 6:
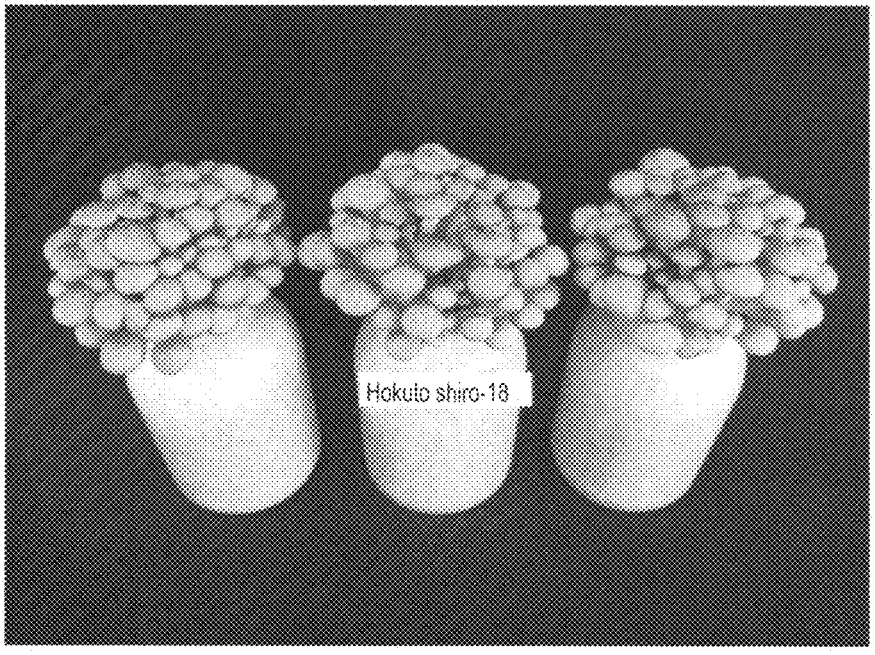
FIG. 6 shows an image of a fruit body of 'Hokuto-18'.

Also, the images of the respective fruit bodies have also been attached. (Refer to FIGS. 4 to 6).

(4) Comparison with 'MH025465' by Dual Culture

Formation of zone line in 'marmo shiro-2' and 'MH025465' were studied by conducting dual culture.

Study Method:

The 'marmo shiro-2' and 'MH025465' were co-inoculated with an interval of 3 cm by using potato dextrose agar culture medium. Then, the formation of zone line was determined by culturing for 28 days at 25° C.

Strain Used:

'marmo shiro-2': Present variety

'MH025465': Parental variety to the present variety

Results:

Zone lines were formed between 'marmo shiro-2' and 'MH025465.' This result shows that 'marmo shiro-2' is different from 'MH025465.' No zone line was seen in the dual culture of 'MH025465 strains.'

(5) Comparison with 'MH025465' by SSR Marker

Applicant verified that 'marmo shiro-2' is different from 'MH025465' by using SSR marker. 'MH025465' do not have the same alleles as 'marmo shiro-2.' This result also shows that 'marmo shiro-2' is different from 'MH025465.'

TABLE 2

| Fungus characteristics Table of *H. marmoreus* (Peck) Bigelow of Recording and Registration | | | |
|---|---|---|---|
| | Present variety | Similar variety | |
| | marmo shiro-2 | Hokuto shiro-1 | Hokuto-18 |
| Physiological property<br>Dual culture | | | |
| Zone line formation | observed | observed | observed |

TABLE 2-continued

Fungus characteristics Table of *H. marmoreus* (Peck) Bigelow of Recording and Registration

| | | | |
|---|---|---|---|
| Dislike-touch reaction | | | |
| Density of hyphae | medium | medium | medium |
| Mycelial growth | medium | medium | medium |
| Color of surface of colony | white | white | white |
| Color of back of colony | pale yellow | pale yellow | pale yellow |
| Accommodativeness for temperature | | | |
| Optimal temperature for hyphal growth (° C.) | 24° C. | 24° C. | 24° C. |
| Hyphal growth rate | | | |
| 5° C./mm | 0.34 mm | 0.41 mm | 0.39 mm |
| 10° C./mm | 1.04 mm | 1.00 mm | 1.14 mm |
| 15° C./mm | 1.87 mm | 1.98 mm | 1.99 mm |
| 20° C./mm | 2.51 mm | 3.07 mm | 2.82 mm |
| 25° C./mm | 2.80 mm | 3.58 mm | 3.13 mm |
| 30° C./mm | 0.28 mm | 0.38 mm | 0.56 mm |
| Morphological property | | | |
| Cap | | | |
| Cross sectional shape | rounding mound | rounding mound | rounding mound |
| Mottle of the surface | few | few | much |
| Size of mottle | small | small | much |
| Distribution of mottle | center | center | whole |
| Clarity of mottle | not clear | not clear | clear |
| Diameter of cap | 17.6 mm | 16.3 mm | 16.9 mm |
| Thickness of cap | 7.8 mm | 7.2 mm | 6.1 mm |
| Color of central area | white 155B | white 155B | grayed-orange 177B |
| | | | grey-brown 199D |
| | Present variety marmo shiro-2 | Similar variety Hokuto shiro-1 | Hokuto-18 |
| Fleshy | medium | medium | medium |
| Gill | | | |
| Color | white 155B | white 155B | yellow-white 158C |
| Alignment | normal | normal | normal |
| Width | medium | medium | medium |
| Density | medium | medium | medium |

TABLE 2-continued

Fungus characteristics Table of *H. marmoreus* (Peck) Bigelow of Recording and Registration

| | | | |
|---|---|---|---|
| Stipe | | | |
| Shape | medium-thick | medium-thick | medium-thick |
| Length | 45.0 mm | 41.8 mm | 50.0 mm |
| Maximum diameter of stipe | 9.0 mm | 9.3 mm | 8.4 mm |
| Color | white NN155C | white NN155C | white NN155C |
| Hair | absent | absent | absent |
| Fleshy | medium | medium | medium |
| Ratio of maximum diameter of stem to diameter just below cap | 1.75 mm | 1.64 mm | 1.56 mm |
| Cultural property | | | |
| Development of fruit body | | | |
| Development | stock | stock | stock |
| Optimal culture period | 81-90 days | 91-100 days | 81-90 days |
| Length of time from fruit body-formation | 21.5 days | 21.3 days | 21.6 days |
| promotion to fruit body harvesting at optimal temperature | | | |
| Optimal temperature for primordial development | 14-16° C. | 14-16° C. | 14-16° C. |
| Optimal temperature for fruit body growth | 14-16° C. | 16-18° C. | 14-16° C. |
| Adaptivity for illuminance | | | |
| Adaptivity for culture | | | |
| Yield | | | |
| Yield of fruit body | 139.3 g | 129.8 g | 141.4 g |
| The number of productive stem | 52.0 | 48.1 | 61.4 |
| Other | | | |
| Bitterness component | | | |
| Disease resistance | | | |
| Contains | | | |

*The employed color chart is R.H.S. Colour Chart, 2007, Fifth edition, prescribed by the Royal Horticultural Society, England.

What is claimed is:

1. A new, distinct variety of Bunashimeji mushroom plant as substantially illustrated and described in the specification.

* * * * *